United States Patent

Tanaka

(10) Patent No.: US 9,194,505 B2
(45) Date of Patent: Nov. 24, 2015

(54) FLOW CHANNEL SWITCHING VALVE

(71) Applicant: SHIMADZU CORPORATION, Kyoto (JP)

(72) Inventor: Shinji Tanaka, Osaka (JP)

(73) Assignee: SHIMADZU CORPORATION, Kyoto (JP)

(*) Notice: Subject to any disclaimer, the term of this patent is extended or adjusted under 35 U.S.C. 154(b) by 80 days.

(21) Appl. No.: 14/196,077

(22) Filed: Mar. 4, 2014

(65) Prior Publication Data

US 2014/0261811 A1    Sep. 18, 2014

(30) Foreign Application Priority Data

Mar. 15, 2013 (JP) ................................. 2013-052989

(51) Int. Cl.
*F16K 11/04* (2006.01)
*F16K 11/074* (2006.01)
*G01N 30/20* (2006.01)

(52) U.S. Cl.
CPC ...... *F16K 11/0743* (2013.01); *G01N 2030/202* (2013.01); *Y10T 137/86501* (2015.04)

(58) Field of Classification Search
CPC .............. F16K 11/074; F16K 11/0743; Y10T 137/86501; Y10T 137/86863; G01N 2030/202
See application file for complete search history.

(56) References Cited

U.S. PATENT DOCUMENTS

| | | | | |
|---|---|---|---|---|
| 3,964,517 A * | 6/1976 | Dickenson | ............... | 137/625.43 |
| 4,550,742 A * | 11/1985 | Stearns | ............................ | 137/14 |
| 5,193,581 A * | 3/1993 | Shiroto et al. | ............ | 137/625.11 |
| 5,529,758 A * | 6/1996 | Houston | ........................ | 422/171 |
| 6,193,213 B1 * | 2/2001 | Stearns et al. | ................ | 251/175 |
| 6,390,127 B2 * | 5/2002 | Schick | ...................... | 137/625.11 |
| 7,096,886 B2 * | 8/2006 | Hofmann | ................. | 137/625.46 |

FOREIGN PATENT DOCUMENTS

JP      2008-215494 A    9/2008

* cited by examiner

*Primary Examiner* — John Fox
(74) *Attorney, Agent, or Firm* — Westerman, Hattori, Daniels & Adrian, LLP

(57) ABSTRACT

A flow channel switching valve includes a stator and a rotor inside an internal space of a housing, and includes a rotor drive portion that rotates the rotor while sliding the rotor on the stator by rotating a rotor drive shaft having, at a forefront, a rotor holding portion that holds the rotor. At a position below the rotor, the housing is provided with a liquid discharge portion that receives liquid leaking from between the stator and the rotor to guide the liquid outside the housing.

4 Claims, 4 Drawing Sheets

FLOW CHANNEL SWITCHING VALVE

BACKGROUND OF THE INVENTION

1. Field of the Invention

The present invention relates to a flow channel switching valve for use in, for example, an auto-sampler that introduces a sample to an analysis flow channel of a liquid chromatograph.

2. Description of the Related Art

As an example, in an auto-sampler that introduces a sample to an analysis flow channel of a liquid chromatograph, after the sample is taken into a sample loop from a sample container, the sample loop is connected to an upstream side of a separation column in the analysis flow channel by switching of a flow channel switching valve, which allows the sample in the sample loop to be transported to a separation column side by a mobile phase flowing in the analysis flow channel.

As the flow channel switching valve for use in the liquid chromatograph, a rotary type switching valve is common. The rotary type switching valve switches a connected flow channel by rotating a rotor (rotary part) (e.g., refer to Unexamined Japanese Patent Publication No. 2008-215494).

In the rotary type switching valve, a plurality of connection ports for connecting flow channel piping are provided in an upper portion of a housing, and a rotor and a stator (stationary part) are contained inside the housing. The rotor and the stator are in contact with each other in a state where planes thereof keep liquid tightness with each other, and the stator is fixed by a pin or the like so as not to rotate with respect to a housing side.

The stator is provided with through-holes corresponding to end portions of flow channels leading to the connection ports in an inner wall surface of the housing, and is fixed to the housing in a state where the through-holes are positioned at the end portions of the flow channels leading to the connection ports. A groove that forms a flow channel selectively connecting between any end portions of the holes of the stator is provided in a surface on a stator side of the rotor, and driving and rotating the rotor while sliding the rotor on the stator changes a position of the groove, thereby switching connection between the connection ports. There is a flow channel switching valve in which the stator is integrated with the housing, and in this case, the configuration is such that the rotor is in contact with a stator portion in the inner wall surface of the housing, and is rotated while sliding on the inner wall surface of the housing.

As described above, in the rotary type flow channel switching valve, since the rotor rotates while sliding on the stator, the rotor and the stator are worn away, thereby deteriorating liquid tightness of a seal surface between the rotor and the stator, so that liquid in a mobile phase may leak from the seal surface. Adhesion of the leaking liquid to mechanical parts such as a drive shaft (shaft) rotating the rotor, a bearing and the like may cause corrosion of these parts, and further the liquid reaching a motor may cause breakdown of the motor.

SUMMARY OF THE INVENTION

An object of the present invention is to prevent liquid leaking from a seal surface between a rotor and a stator from adhering to a drive system of the rotor.

A flow channel switching valve according to the present invention includes a housing that has an internal space and includes connection ports connecting flow channel piping in an outer surface, the connection ports leading to the internal space through flow channels. Inside the internal space of the housing, a stator and a rotor are provided.

The stator has a plane fixed to the housing to form one wall surface of the internal space. In the plane, a plurality of connection holes are provided, which are end portions of the flow channels leading the connection ports to the internal space.

The rotor is arranged inside the internal space of the housing so as to come into contact with the plane of the stator where the connection holes are provided while keeping liquid tightness, and is provided with a groove in a surface in contact with the stator, the groove forming a flow channel selectively connecting any one pair of the connection holes.

The flow channel switching valve includes a rotor drive shaft having, at a forefront, a rotor holding portion that holds the rotor. The rotor is held by the rotor holding portion of the rotor drive shaft. The rotor drive shaft is arranged perpendicular to the plane of the stator where the connection holes are provided. The rotor drive shaft is rotated to thereby rotate the rotor while sliding the rotor on the stator.

Furthermore, the flow channel switching valve includes a depressed portion receiving liquid at a position below the rotor inside the housing, and an opening provided in the housing to guide the liquid received by the depressed portion outside the housing.

Since the flow channel switching valve of the present invention is provided with the depressed portion receiving the liquid at the portions below the rotor inside the housing, and the opening provided in the housing to guide the liquid received in the depressed portion outside the housing, the liquid leaking from between the stator and the rotor can be collected and discharged outside the housing, and the liquid can be prevented from moving along the rotor drive shaft and reaching a drive system such as a motor of a rotor drive mechanism.

DETAILED DESCRIPTION OF THE INVENTION

In the present invention, a projected portion that is projected from an inner wall surface of a housing toward a rotor holding portion to surround an outer circumference of the rotor holding portion may be included, and a depressed portion receiving liquid in a surface on a stator side of the projected portion may be provided. The above-described structure enables the depressed portion receiving the liquid to be provided without making a structure of the flow channel switching valve complicated. Since in this structure, the depressed portion is provided in a periphery of the rotor holding portion, the liquid can be prevented from reaching a base end side with respect to the rotor holding portion of a rotor drive shaft.

Furthermore, it is preferable that on the projected portion, a ring-shaped seal member is provided that comes into close contact with a circumferential surface of the rotor holding portion to seal a clearance between the rotor holding portion and the projected portion, and that the depressed portion receiving the liquid is provided at a position along an outer circumference of the seal member. This can prevent the liquid from flowing from the clearance between the rotor holding portion and the projected portion to the base end side of the rotor drive shaft.

Furthermore, it is preferable that a surface on the stator side of the seal member is inclined so as to guide the liquid to a depressed portion side. This enables the liquid leaking from between the stator and rotor to be efficiently collected in the depressed portion, and can more surely prevent the liquid from reaching the drive system of the rotor.

Figure 1:
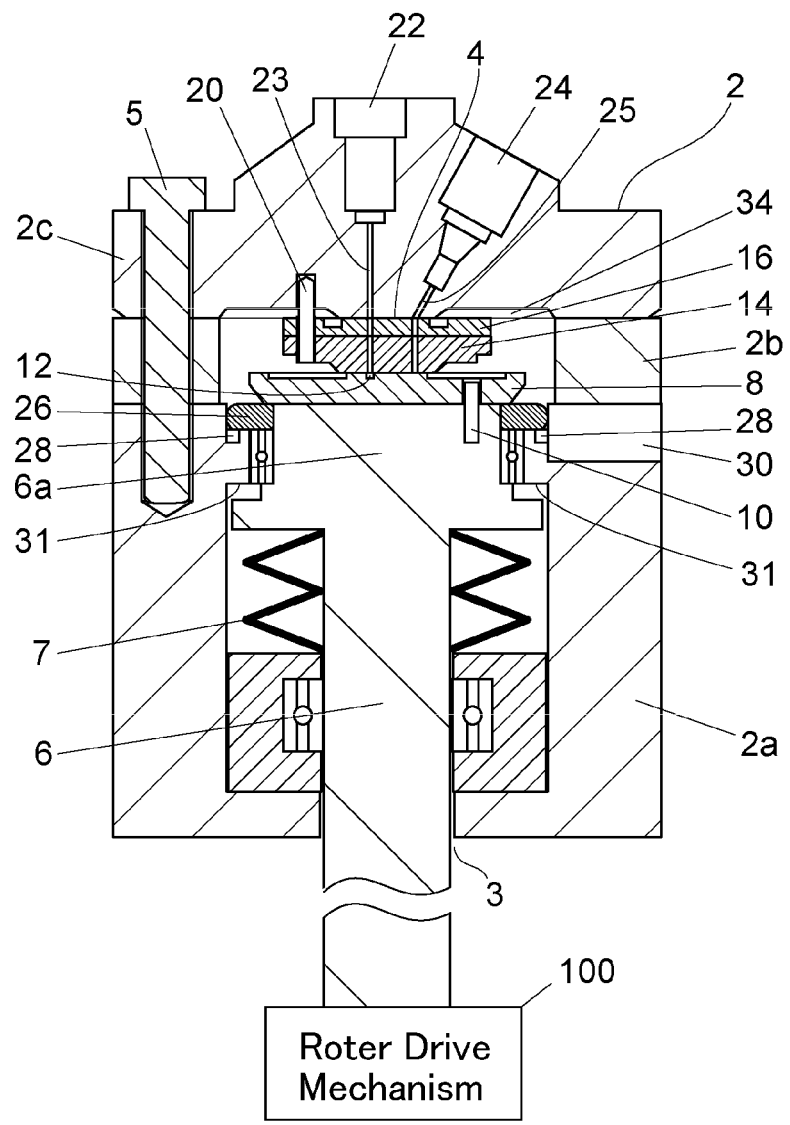
FIG. 1 is a cross-sectional view showing one embodiment of a flow channel switching valve.
Figure 3:
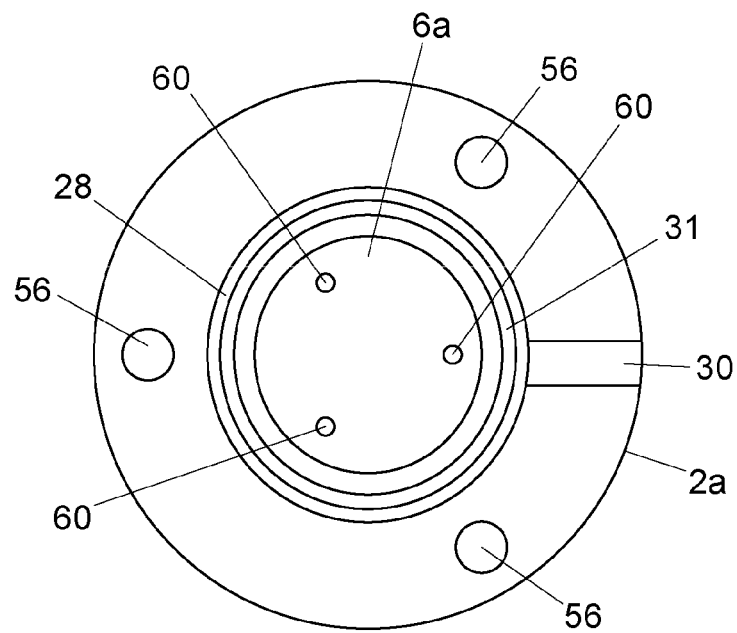
FIG. 3 is a plane view of the housing body side of the same embodiment as seen from above in a state where a rotor and a seal ring are detached.

One embodiment of a flow channel switching valve will be described with reference to FIGS. 1 and 3.

First, a structure of the same embodiment will be described with reference to FIG. 1.

In an internal space of a housing 2, a rotor 8 as a rotary part, and a stator 14 as a stationary part are contained. The housing 2 is circular in a planar shape, and includes a plurality of connection ports 22, 24 connecting flow channel piping in an upper outer surface. In a central portion of a lower surface of the housing 2, a hole 3 is provided, and a rotor drive shaft 6 making up a part of a rotor drive portion that rotates the rotor 8 penetrates the hole 3. The rotor drive shaft 6 is supported rotatably by a bearing inside the housing 2, and is coupled to a rotor drive mechanism 100 that rotates the rotor drive shaft 6 outside the housing 2. The rotor drive shaft 6 and the rotor drive mechanism 100 make up a rotor drive portion.

The housing 2 is made up of three members of a housing body 2a, an intermediate member 2b, and a housing top 2c. The housing body 2a has a cylindrical shape, and the hole 3 is opened at a center of a seating surface. In a state where an opening of the housing body 2a is in an upward direction, the ring-shaped intermediate member 2b is placed on the opening, and the disc-shaped housing top 2c is placed on the intermediate member 2b. The housing body 2a serves as a base for the housing 2, and the intermediate member 2b and the housing top 2c are detachably attached to the housing body 2a by bolts 5. The bolts 5 are fastened so as to penetrate the intermediate member 2b from an upper surface side of the housing top 2c located in an upmost portion of the housing 2 and reach the housing body 2a. The housing top 2c is provided with through-holes through which the bolts 5 penetrate the housing top 2c, and the intermediate member 2b is also provided with through-holes 54 through which the bolts 5 penetrate the intermediate member 2b (refer to FIG. 2). The housing body 2a is provided with screw holes 56 to fasten the bolts 5 (refer to FIG. 2). Although in FIG. 1, only one of attachment positions of the bolts 5 is illustrated, the bolts 5 are attached at three even positions in a circumferential edge portion on a plane viewed from an upper surface side of an upper surface of the housing top 2c. The attachment positions of the bolts 5 are not limited thereto.

In a lower surface of the housing top 2c, which is an inner wall surface of the housing 2, a flow channel connection portion 4 is provided. The flow channel connection portion 4 is a plane where holes of end portions of flow channels 23, 25 leading to the connection ports 22, 24 are arrayed, and the stator 14 is in contact with the flow channel connection portion 4 with a packing 16 interposed. The flow channel connection portion 4 is a circular plane region with an outer circumference surrounded by a ring-shaped depression 34. The stator 14 and the packing 16 are each a circular member larger than the flow channel connection portion 4 in a planar shape, and a central portion of the packing 16 is in contact with the flow channel connection portion 4 while keeping liquid tightness.

In the packing 16, through-holes are provided respectively corresponding to the holes of the end portions of the flow channels 23, 25 arranged in the flow channel connection portion 4, and similarly, in the stator 14, there are also provided through-holes. The stator 14 and the packing 16 are fixed to the housing top 2c side in a state where these through-holes are positioned at the holes of the end portions of the flow channels 23, 25 and the like in the housing top 2c. In the housing top 2c, a hole 36 into which a stator fixing pin 20 is inserted is provided, and in the stator 14 and the packing 16, through-holes through which the stator fixing pin 20 penetrates the stator 14 and the packing 16, respectively are provided, so that inserting the stator fixing pin 20 prevents the stator 14 and the packing 16 from rotating.

The rotor 8 is rotated by the rotor drive shaft 6 inside the housing 2. The rotor drive shaft 6 is arranged perpendicular to the plane of the flow channel connection portion 4, and is provided with a rotor holding portion 6a at a forefront. A forefront surface of the rotor holding portion 6a is a plane parallel to the flow channel connection portion 4, and the rotor 8 is in contact with the stator 14 by being held by the forefront surface of the rotor holding portion 6a. A base end portion of the rotor drive shaft 6 is led outside the housing 2 through the hole 3 of the housing 2 to be rotated around a shaft center thereof by the rotor drive mechanism 100 including a rotation mechanism such as a motor and the like outside the housing 2. The rotor holding portion 6a and the rotor 8 are fixed by a rotor fixing pin 10 in a rotation direction, and the rotor 8 is rotated by the rotation of the rotor drive shaft 6. The rotor 8 is provided with a through-hole 58 through which the rotor fixing pin 10 penetrates the rotor 8, and the rotor holding portion 6a is provided with a hole 60 into which the rotor fixing pin 10 is inserted (refer to FIG. 2).

In the rotor drive shaft 6, the rotor holding portion 6a at the forefront portion has a larger outer diameter than that of a shaft portion on the base end side. A spring 7 in a compressed state is inserted between a bottom portion of the housing body 2a and the rotor holding portion 6a, and the rotor drive shaft 6 is biased to the housing top 2c side by the spring 7. This allows the rotor 8 to be pressed to the stator 14. In a surface on the stator 14 side of the rotor 8, a groove 12 is provided that forms a flow channel connecting flow channels of any one pair of the plurality of flow channels 23, of the housing top 2c, and a position of the groove 12 is changed by the rotation of the rotor 8.

When the rotor drive shaft 6 is rotated by the rotor drive mechanism 100, the position of the groove 12 is changed to switch the connection between the plurality of flow channels 23, 25 of the flow channel housing top 2c.

Figure 2:
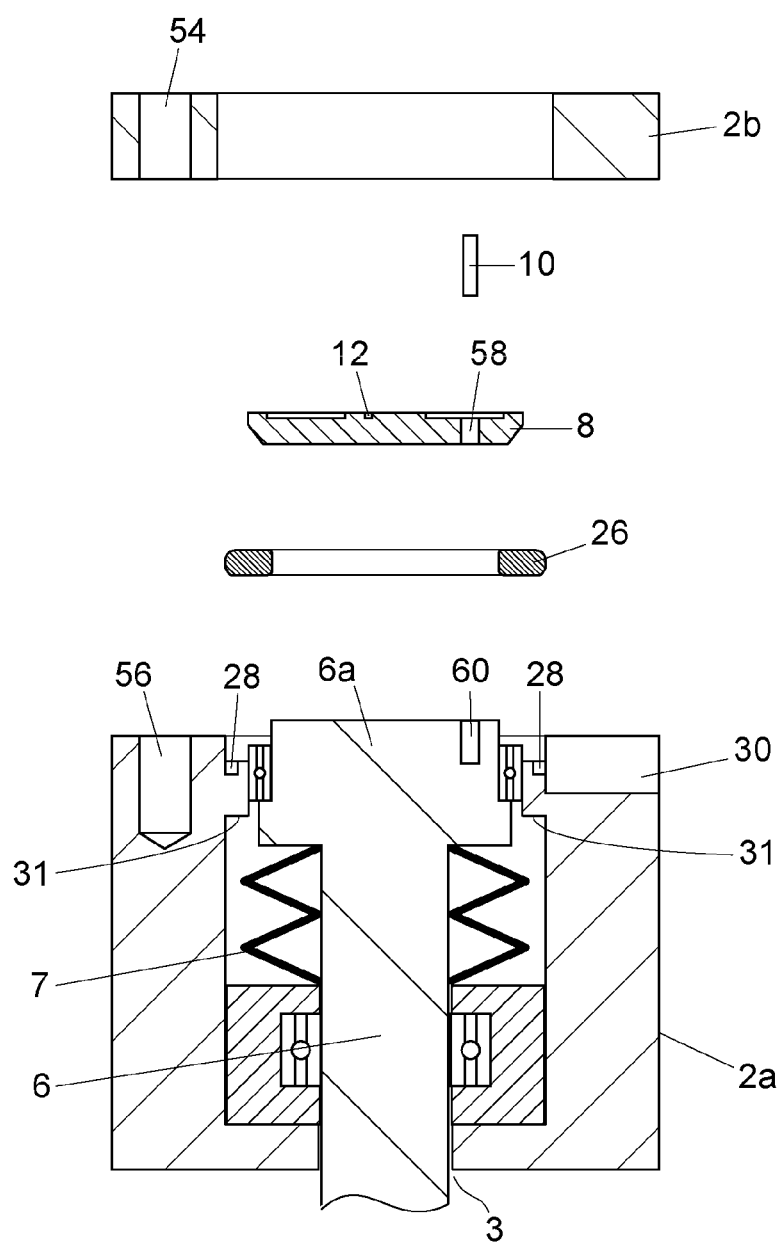
FIG. 2 is an exploded cross-sectional view of a housing body side of the same embodiment.
Figure 4:
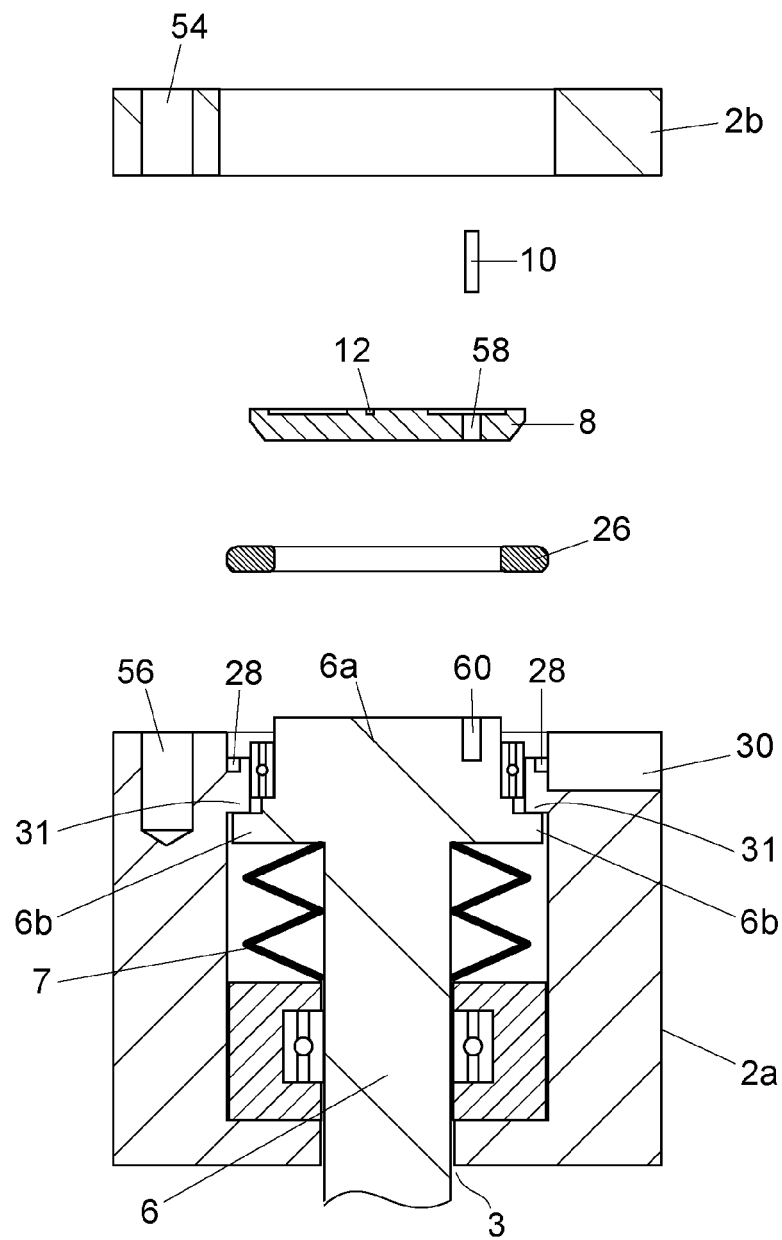
FIG. 4 is an exploded cross-sectional view of the housing body side showing another embodiment of the flow channel switching valve.

A structure of a housing body 2a side will be further described with reference to FIG. 1 and FIGS. 2 and 3. FIG. 3 is an exploded cross-sectional view of the housing body side, and FIG. 4 is a plane view of the housing body side as seen from above in a state where the intermediate member and the seal ring are detached.

A projected portion 31 is provided having a rectangular cross section that is projected in a ring shape along an inner circumferential surface on the housing top 2c side of the housing body 2a. An inner diameter of the portion where the projected portion 31 is provided is slightly larger than an outer diameter of the rotor holding portion 6a, and the projected portion 31 surrounds an outer circumference of the rotor holding portion 6a with a slight clearance. The rotor holding portion 6a holds the rotor 8 above the projected portion 31.

A ring-shaped seal ring 26 (the seal member) is arranged between the inner circumferential surface of the housing body 2a and an outer circumferential surface of the rotor holding portion 6a at a position above the projected portion 31. The seal ring 26 tightly adheres to the outer circumferential surface of the rotor holding portion 6a to seal the clearance between the rotor holding portion 6a and the projected portion 31. A material of the seal ring 26 is a resin such as, for example, PDMS (polydimethylsiloxane) and PTFE (polytetrafluoroethylene).

In an upper surface of the projected portion 31, a ring-shaped groove 28 (the depressed portion) with a top open is provided along the inner circumferential surface of the housing body 2a at a border portion with the inner circumferential surface of the housing body 2a. At one position of an end surface on the housing top 2c side of the housing body 2a, a groove 30 is provided forming an opening, which leads the groove 28 outside the housing 2 (refer to FIG. 3). The groove 28 collects liquid leaking from between the rotor 8 and the stator 14 to guide the liquid to the groove 30, and the groove 30 discharges the liquid guided by the groove 28 outside the housing 2.

Since the seal ring 26 is in contact with the upper surface of the projected portion 31, the liquid leaking from between the rotor 8 and the stator 14 moves along an upper surface of the seal ring 26. Since the seal ring 26 tightly adheres to the outer circumferential surface of the rotor holding portion 6a, the liquid does not enter between the seal ring 26 and the rotor holding portion 6a, and the leaking liquid moves to an inner circumferential surface side of the housing body 2a along the upper surface of the seal ring 26. At the position just below a circumferential edge portion of the seal ring 26, the groove 28 is provided, and the liquid that reaches the circumferential edge portion of the seal ring 26 is guided to the groove 30 by the groove 28, thereby being discharged outside the housing 2.

In order to make it easy to collect, in the groove 28, the liquid leaking out onto the upper surface of the seal ring 26, an outer side of the upper surface of the seal ring 26 is inclined so as to moderately decline toward the circumferential edge portion. While in FIGS. 1 and 2, the outer side of the seal ring 26 has a rounded shape, a shape of the seal ring 26 may be any shape that can bring about an effect of making it easy to guide the liquid to the groove 28, such as a tapered shape on the outer side of the upper surface of the seal ring 26.

The structure in which the liquid leaking from between the rotor 8 and the stator 14 is discharged outside by the groove 28 and the groove 30 can be applied to not only the flow channel switching valve in which the stator 14 is configured integrally with the housing top 2c but also a flow channel switching valve having a different structure from the flow channel switching valve of this embodiment.

As shown in FIG. 4, the rotor holding portion 6a may include a projected portion 6b that is projected in a flange shape along the outer circumferential surface in a lower portion of the rotor holding portion 6a. The outer diameter of the portion of the rotor holding portion 6a where the projected portion 6b is provided is made larger than the inner diameter of the portion where the projected portion 31 of the housing body 2a is provided. Thereby, although the rotor drive shaft 6 tries to rise by an elastic force of the spring 7 when the housing top 2c is detached from the housing body 2a, the projected portion 6b of the rotor holding portion 6a is engaged with a lower surface of the projected portion 31 of the housing body 2a, so that the rotor drive shaft 6 stops at a position where the rotor drive shaft 6 rises up to a predetermined height.

The projected portion 6b and the projected portion 31 are provided with a positional relation in which they do not interfere with each other in a state where the housing top 2c is mounted on the housing body 2a, and it is not until the housing top 2c is detached from the housing body 2a and the rotor drive shaft 6 rises to the predetermined height that they interfere with each other. The predetermined height is a height before the spring 7 completely returns to the natural length. This reduces a loosening amount of bolts needed when the housing top is detached from the housing body, and a fastening amount of the bolts needed when the housing top is attached to the housing body, which makes it easy to evenly loosen or fasten the respective bolts, and makes easy the attachment/detachment of the housing top with respect to the housing body.

What is claimed is:

1. A flow channel switching valve comprising:
   a housing that has an internal space, and includes connection ports connecting flow channel piping in an outer surface, the connection ports leading to the internal space through flow channels;
   a stator that is provided inside the internal space of the housing, has a plane fixed to the housing to form one wall surface of the internal space, and is provided with a plurality of connection holes in the plane, the plurality of connection holes being end portions of the flow channels leading the connection ports to the internal space;
   a rotor that is arranged inside the internal space so as to come into contact with the plane of the stator where the connection holes are provided while keeping liquid tightness, and is provided with a groove in a surface in contact with the stator, the groove forming a flow channel selectively connecting any one pair of the connection holes;
   a rotor drive portion that includes a rotor drive shaft having, at a forefront, a rotor holding portion that holds the rotor, and is arranged perpendicular to the plane of the stator where the connection holes are provided, the rotor drive portion rotating the rotor drive shaft to thereby rotate the rotor while sliding the rotor on the stator;
   a depressed portion receiving liquid at a position below the rotor inside the housing; and
   an opening provided in the housing to guide the liquid received by the depressed portion outside the housing.

2. The flow channel switching valve according to claim 1, comprising a projected portion that is projected from an inner wall surface of the housing toward the rotor holding portion to surround an outer circumference of the rotor holding portion, and is provided with the depressed portion in a surface of the projected portion on a side of the stator.

3. The flow channel switching valve according to claim 2, wherein a ring-shaped seal member is provided on the projected portion, the seal member coming into close contact with a circumferential surface of the rotor holding portion to seal a clearance between the rotor holding portion and the projected portion, and
   the depressed portion is provided along an outer circumference of the seal member.

4. The flow channel switching valve according to claim 3, wherein a surface of the seal member on the side of the stator is inclined so as to guide the liquid to a side of the depressed portion.

* * * * *